United States Patent [19]
Martin et al.

[11] 3,991,425
[45] Nov. 16, 1976

[54] PROSTHETIC BONE JOINT DEVICES

[75] Inventors: Lawrence L. Martin, Hugo; Robert C. Westerberg, St. Paul, both of Minn.

[73] Assignee: Minnesota Mining and Manufacturing Company, St. Paul, Minn.

[22] Filed: Nov. 20, 1975

[21] Appl. No.: 633,942

[52] U.S. Cl. .................................. 3/1.91; 128/92 C
[51] Int. Cl.² ........................................... A61F 1/24
[58] Field of Search .......................... 3/1.9–1.911, 3/1, 12.6, 12.7; 128/92 C

[56] References Cited
UNITED STATES PATENTS

| | | | |
|---|---|---|---|
| 3,314,420 | 4/1967 | Smith et al. | 128/92 C |
| 3,466,669 | 9/1969 | Flatt | 3/1.91 |
| 3,651,521 | 3/1972 | Devas | 3/1.91 |
| 3,656,186 | 4/1972 | Dee | 3/1.91 |
| 3,765,033 | 10/1973 | Goldberg et al. | 3/1.911 |
| 3,946,445 | 3/1976 | Bentley et al. | 3/1.91 |

FOREIGN PATENTS OR APPLICATIONS

| | | | |
|---|---|---|---|
| 939,226 | 2/1956 | Germany | 128/92 C |

*Primary Examiner*—Ronald L. Frinks
*Attorney, Agent, or Firm*—Alexander, Sell, Steldt & Delahunt

[57] ABSTRACT

A surgically implantable prosthetic joint replacement device formed preferably of ceramic and having mating concave and convex condylar surfaces and intersecting lands for stopping motion at extended and contracted positions of the joint. The device consists of male and female portions for implantation in medullary canals of metacarpals and/or phalanges and having grooves along the dorsal surfaces for reception of extensor tendons. Engagement of the parts permits rotation and hyperextension.

5 Claims, 7 Drawing Figures

PROSTHETIC BONE JOINT DEVICES

This invention relates to surgically implantable prosthetic joint replacement devices and particularly devices adapted to replacement of interphalangeal and metacarpo-phalangeal joints as, for instance, in cases of severe accidental damage or advanced disease such as rheumatoid arthritis, ankylosis, etc.

The replacement of joints of the hand has been found to be an effective method for combatting the crippling effects of advanced arthritis of certain types and for relieving pain associated with such conditions. An extensive medical literature has developed parallel to the patent literature in which numerous devices are described. Such devices are generally either single bodies or two parts which are hinged together or articulate with one another. One piece prosthetic devices composed of elastomer, such as silicone rubber, are described in U.S. Pat. Nos. 3,462,765; 3,593,342 and 3,681,786. These appear to be suitable as long as the integrity of the device is retained but may be subject to mechanical fatigue in time. Fracture has been reported in the medical literature. A two part hinged metallic device is described in U.S. Pat. No. 3,466,669. Both types of prosthesis suffer from a longitudinal rigidity such that there is no lengthwise "play" or "give" i.e., hyperextension. Longitudinal stresses can result in loosening the attachment of such devices to the bones which may be objectionable. Other devices employ two parts having a hingelike rotatability as the result of locking a head of one part in a suitable cavity of the other part. Exemplary devices are described in U.S. Pat. Nos. 3,506,982, 3,805,302 and British Patent No. 1,304,837. Such devices may exhibit some hyperextension.

It is an object of this invention to provide a two part joint prosthesis having substantial freedom from mechanical fatigue and permitting small longitudinal hyperextension without loss of function. Other objects will become evident herein elsewhere.

In accordance with these and other objects of the invention an implantable prosthesis is provided consisting of two interengaging parts. For convenience the parts are termed male and female. Either male or female part or member may be proximal under desired conditions of implantation, or alternatively either may be distal. Each part is characterized by (1) a shank having a central axis for insertion in the medullary canal of a bone and (2) a head or condylar portion at one end of the axis with grooved dorsal surface. The female head portion bears two condyles with convex condylar surfaces embracing a circular arc of greater than 180° around a center of curvature with an intercondylar space between the condyles including two lands at an angle of about 135° to each other one of which is at right angles to the central axis of the shank and the dorsal surface of the head and dorsal to the center of curvature of the condylar surfaces and the other of which is palmar or volar to said center and to the said axis and inclines backward toward the shank. The male head portion thus bears an oblique angled interdigitating portion adapted to engage the space between the intercondylar space of the female head piece with predetermined lateral fit with a tolerance of up to about 0.2 mm. Finishing operations, e.g. polishing, will usually permit a degree of tolerance and will also tend to round off or chamfer sharp edges and external corners and fillet internal angles. The line of intersection of the two lands of the male head is the center of curvature for two concave condylar surfaces forming a circular arc of greater than 180° on either side of the interdigitating portion. The intersecting lands of the interdigitating portion of the male head portion and in the intercondylar space of the female head portion are at an oblique angle to control rotation of the joint. The lands at right angles to the axis of the shank stop motion when the axes of the parts are in an extended position (180°) and the other land at an angle of about 135° and toward the shank portion stop motion in a position where the prosthesis is flexed to about 90°. The dorsal surfaces of the head portions are grooved to receive the appropriate extensor tendon which together with retained ligaments and flexor tendons serve to hold the two portions of the prosthesis in alignment. Excessive hyperextension can result in dislocation or subluxation but resetting should be possible as with any normal joint which is dislocated by hyperextension.

In general, a prosthesis for the metacarpo-phalangeal joint requires a slight offset of the axis of rotation from the axis of the shank portion e.g., the centers of curvature of the condylar surfaces of the members are palmar to the axes of the shanks. This is of the order of magnitude of about a millimeter or less to about 3 mm. or slightly more and will, of course, depend on the size of the joint being replaced. The female member of metacarpo-phalangeal joints is inserted in the metacarpal to minimize palmar subluxations. For interphalangeal joints, the center of curvature of condylar surfaces lies in a plane with the axis of the shank portion.

Prosthetic devices of the invention can be made of metals compatible with the human body, e.g. surgical stainless steel (Type 316-L) or surgical cobalt-chrome alloy, but preferably are made from a hard ceramic such as high purity alumina and more preferably a high purity alumina with at least 95% of theoretical density and with highly polished mating bearing surfaces that are finished to less than about 10 RMS. The shank portions are advantageously provided with porous ceramic coating so that the shanks are susceptible to penetration by bone growth and thereby to becoming thoroughly bonded in the medullary canals. Cementing may also be employed if desired.

The shank portions may be of square, rectangular, round, triangular or other convenient cross-section as is considered most convenient to the particular surgical problem. Thus in a metacarpal having a somewhat rectangular medulla a rectangular cross-section may be advantageous although fitting of round shapes may be easier in the phalanges. Likewise the head portions may be of generally cylindrical or spherical shape if desired or with an essentially rectangular outline as viewed from the end. In any case, it is usually desirable to provide a right-angled shoulder at the point where shank and head join so that surgical implantation will be simplified by requiring a right-angle cut at the end of the bone to align the joint correctly. Coating of the shank to permit intergrowth of bone may be desirable and postoperative measures to assure minimal resorption of bone are of course needed.

Surgical implantation requires dissection to reveal the joint and resection of the bones as necessary to fit the prosthesis. The extensor tendon is suitably held away from the site when the prosthesis is introduced. The extensor tendon is finally placed in the dorsal groove of the prosthesis followed by closing of the incision. The procedure for introduction of a one piece prosthetic device is described generally in Air Instrument Surgery compiled by R. M. Hall, Vol. 3, Facial, Oral and Reconstructive Surgery, pp. 146–156 (Springer Verlag, Berlin, Heidelberg, N.Y., 1973). Immobilization of the joints or padding during the postoperative period may be provided if deemed necessary by the surgeon. It is contemplated that the highly polished joint will operate for prolonged periods with no lubrication other than serous fluids of the body which may seep into the joint and thereby simulate synovial fluids. The low solubility and great hardness and strength of alumina minimize deterioration of the joint for long periods of time.

The invention is now further illustrated by reference to the drawings herewith. Where FIG. 1 is diagrammatic view of a left forefinger showing implanted prostheses of the invention.

Figure 1:
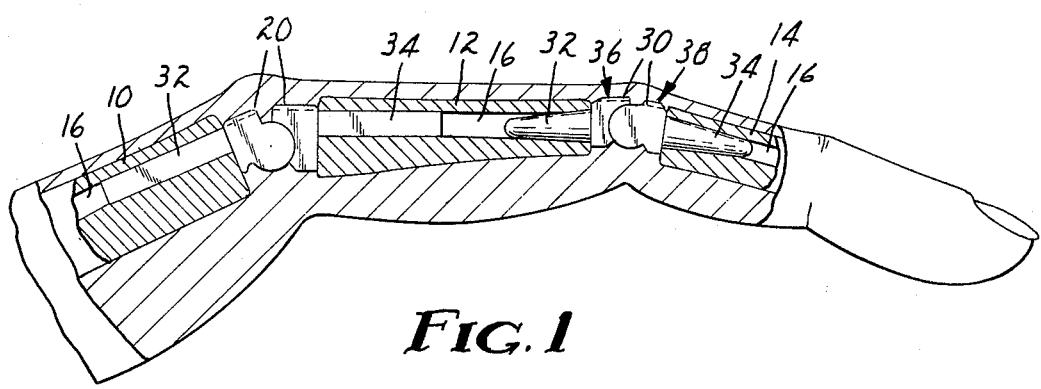

The forefinger shown in FIG. 1 is diagrammatic and does not attempt to show musculature, innervation or vascularization. All drawings are at approximately double natural size for an adult but it will be appreciated that prosthesis of a range of sizes are contemplated and will be needed.

In FIG. 1 it will be seen that prosthesis 20 with shanks 32 and 34 is positioned in medullary canals 16 of metacarpal 10 and proximal phalanx 12 the ends of each of which have been resected. It is contemplated that resection may not always be required to the extent here shown. Further it is seen that prosthesis 30 with shanks 32 and 34 in medullary canals 16 replaces the proximal interphalangeal joint between proximal phalanx 12 and medial phalanx 14.

Figure 2:
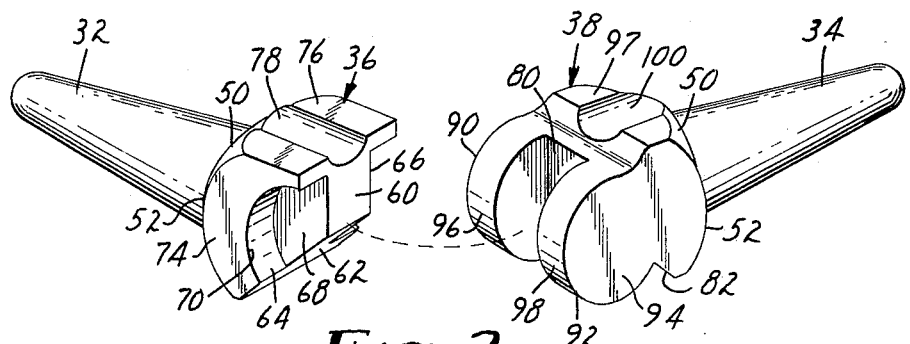
FIG. 2 is an exploded and partially rotated view of an interphalangeal prosthesis of the invention.
Figure 3:
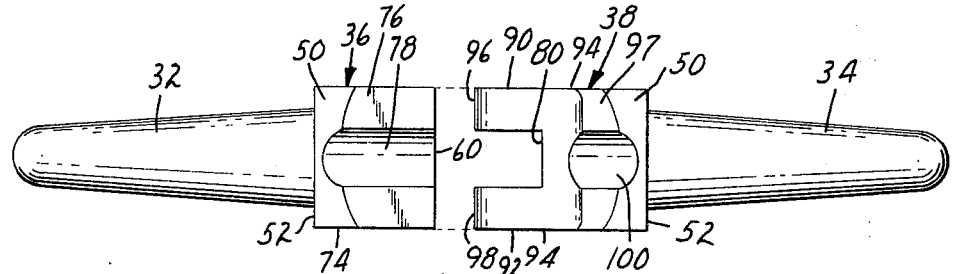
FIGS. 3 and 4 are dorsal and lateral views of the prosthesis of FIG. 2.
Figure 4:
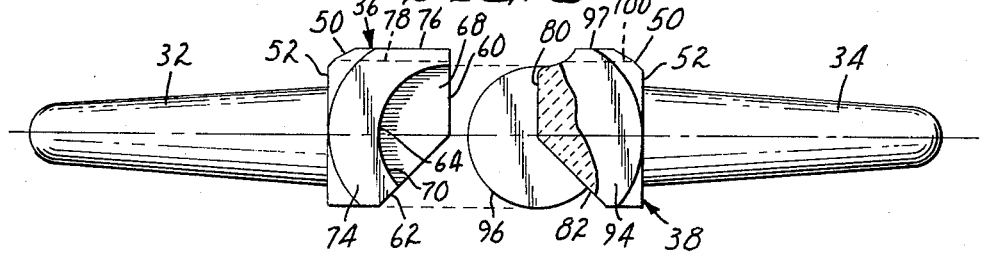

Prosthesis 30 is shown in greater detail in FIGS. 2, 3 and 4. The male head 36 and female head 38 are shown with partially spherical curvatures 50 rear surfaces 52 at the juncture with shanks 32 and 34. This curvature is optional and may be to a considerably greater radius of curvature than here shown so that only sharp curves and edges are rounded.

Male head 36 has land 60 at right angles to the axis of shaft 32 and to dorsal surface 76 and intersecting land 62 at an angle of about 135° to land 60 and running rearwards toward the shank. Recesses 64 and 66 leave interdigitating or engaging projection 68 with concave condylar surfaces 70 (the rearward surface the mirror image of that seen is only noted in FIG. 3). The center of curvature of concave condylar surfaces 70 is at the intersection of lands 60 and 62. Lateral faces 74 may be flat as shown or may be curved to provide better simulation of the replaced joint as desired. The dorsal surface 76 of the male head is provided with groove 78 for reception of the extensor tendon. The overall arrangement of surfaces may provide any convenient or desirable structure.

Female head 38 has land 80 at right angles to the axis of shaft 34 and to dorsal surface 97 and intersecting land 82 at an angle of about 135° to land 80 and running rearwards toward shank 34 as seen in FIG. 4. Lands 80 and 82 are included between condyles 90 and 92 (92 is broken away in FIG. 4 to show the included intersecting lands) which condyles have lateral faces 94 and convex condylar surfaces 96 and 98 having a center of curvature at the intersection of lands 80 and 82. Dorsal surface 97 of the female head is provided with groove 100 for reception of the extensor tendon. It will be seen that condylar surfaces 96 and 98 are more than semicircular and are curved up toward dorsal surface 97.

Figure 5:
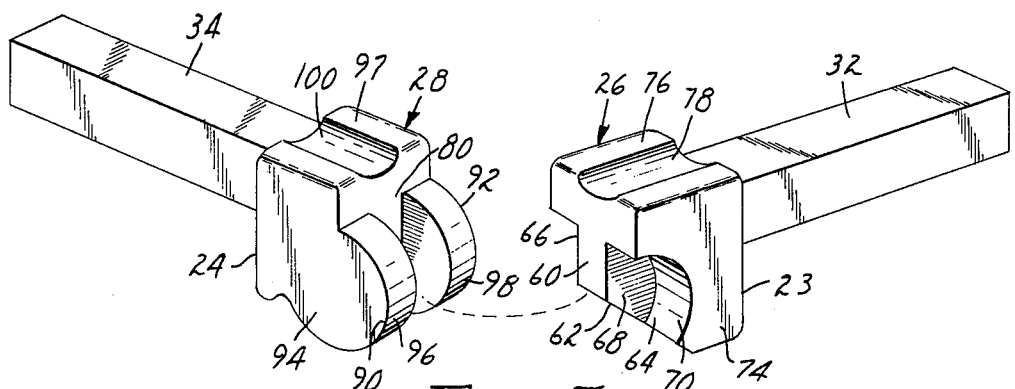
FIG. 5 is an exploded and partially rotated view of a metacarpo-phalangeal prosthesis of the invention.
Figure 6:
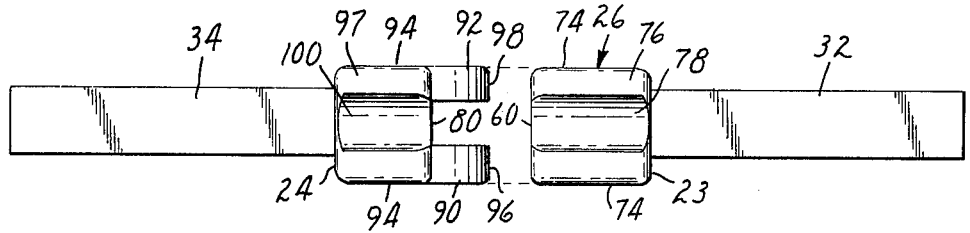
FIGS. 6 and 7 are dorsal and lateral views of the prosthesis of FIG. 5.
Figure 7:
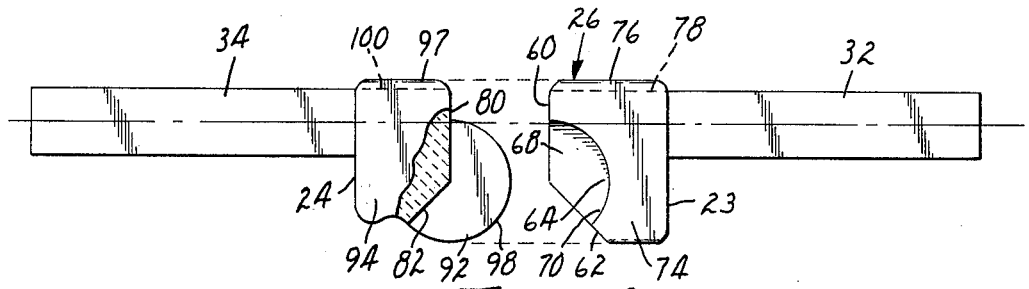

Prosthesis 20 is shown in greater detail in FIGS. 5, 6 and 7. Parts are numbered as in FIGS. 2–4 insofar as possible. The male head 26 and female head 28 are shown with rearward surfaces 23 and 24 at the point of juncture with shanks 32 and 34 at right angles to the axes of the shanks. Corners and edges of the heads are rounded (not numbered) as implantation of sharp edged objects is generally undesirable. The edges of the shanks are preferably rounded to avoid excessive force on the bones which can result in splitting of bones.

Male head 26 in FIGS. 5, 6 and 7 has land 60 at right angles to the axis of shaft 32 and intersecting land 62 at an angle of about 135° to land 60 and running rearwards toward the shank. Recesses 64 and 66 leave interdigitating part 68 with concave condylar surface 70 (one not visible) having a center of curvature at the intersection of lands 60 and 62. In this embodiment this intersection is offset in the palmar or volar direction from the axis of the shank. Lateral faces 74 and dorsal surface 76 may be flat as shown or curved to greater or less extent. Dorsal surface 76 is provided with groove 78 for reception of the extensor tendon.

Female head 28 in FIGS. 5, 6 and 7 has land 80 at right angles to the axis of shaft 34 and intersecting land 82 at an angle of about 135° to land 80 and running rearwards toward shanks 34 as seen in FIG. 7. The intersection of lands 80 and 82 is offset in the palmar direction from the axis of shank 34 as also seen in FIG. 7. Lands 80 and 82 are included between condyles 90 and 92 (90 is broken away in FIG. 7 to show the intersecting lands) which condyles have lateral faces 94 and convex condylar surfaces 96 and 98 having a center of curvature at the intersection of lands 80 and 82 and a circular arc of over 180°. Dorsal surface 97 is provided with groove 100 for reception of the extensor tendon.

What is claimed is:

1. An implantable prosthetic bone joint device consisting essentially of mutually engageable male and female members each having an elongated shank portion with axis, said shank portion being for engagement in the medullary canal of a bone, and each further having a head portion with a grooved dorsal surface and comprising lands intersecting at about 135°, a first land being at right angles to the axis of the shank portion and the said dorsal surface and the second being directed backwards toward the shank portion, the female head further having two condyles with convex condylar surface of greater than 180° of arc one on either side of said lands and extending beyond said first land forming an intercondylar space therebetween and with center of curvature of said surfaces at the line of intersection of said lands and the male head having two concave condylar surfaces one on either side of said lands and with center of curvature at the line of intersection of said lands, said lands thereby extending beyond said condylar surfaces and forming a projection engaging with the intercondylar space of said female head.

2. The implantable prosthetic bone joint device according to claim 1 wherein prolongation of the axis of the shank passes through the line of intersection of the lands.

3. The implantable prosthetic bone joint device according to claim 1 wherein prolongation of the axis of the shank passes on the dorsal side of the line of intersection of the lands.

4. The implantable prosthetic bone joint device according to claim 1 wherein the projection of the male head engages the space between the condyles of the female head with a clearance of up to about 0.2 mm. whereby slight lateral movement of said joint is provided.

5. The implantable prosthetic bone joint device according to claim 1 wherein the material of the device is alumina of at least 95% density and bearing surfaces are finished to less than about 10 RMS.

* * * * *